United States Patent [19]

Sugihara et al.

[11] Patent Number: 5,780,509
[45] Date of Patent: Jul. 14, 1998

[54] COMPOUND BEARING TWO, 2,6-DIIODOPHENOL-4-YL GROUPS AND DIAGNOSTIC DRUG FOR IODINE ALLERGY

[75] Inventors: Yoshiki Sugihara, Tsukuba; Hiroshi Shionoya, Tokorozawa; Kiyomi Yamatsu, Kamakura, all of Japan

[73] Assignee: Muromachi Kagaku Kogyo Kaisha, Ltd., Japan

[21] Appl. No.: 737,625

[22] PCT Filed: May 24, 1995

[86] PCT No.: PCT/JP95/00997

§ 371 Date: Jan. 29, 1997

§ 102(e) Date: Jan. 29, 1997

[87] PCT Pub. No.: WO95/32173

PCT Pub. Date: Nov. 30, 1995

[30] Foreign Application Priority Data

May 24, 1994 [JP] Japan .................................. 6-109374

[51] Int. Cl.$^6$ .................. A61K 31/195; C07C 229/24
[52] U.S. Cl. .................. 514/563; 514/2; 514/5; 514/616; 514/559; 530/300; 530/329; 530/331; 554/36; 554/37; 562/433; 564/153
[58] Field of Search .................. 564/152, 153, 564/155, 157; 424/9.451, 9.452; 514/616

[56] References Cited

FOREIGN PATENT DOCUMENTS 3-120296  5/1991  Japan .

OTHER PUBLICATIONS

Immunology, Roitt et al pp. 264–265.
Synthesis and Applications of Isotopically Labeled Compounds Proceedings of an International Symposium,Heys et al Jun. 1982 pp. 425–426 Preparation of Tritiated Diethylstilbestrol and Related Compounds.
Experientia (1985), 41 (3), pp. 385–387 Bernard et al IgG purification to measure the level of an iodinated thyroglobulin etc.
Khim, Prom–st. (Moscow) 1989, (2), pp. 106–109.
Analytical Biochemistry 210, 129–135 (1993) Tsomides et al Stoichiometric Labeling of Peptides by Iodination on Tyrosyl or Histidyl Residues.
J. of Labelled Compounds and Radiopharmaceuticals vol. XVII, No. 6 pp. 901–909 Maurizis et al Marquage A Haute Activitie Specifique etc.

*Primary Examiner*—Shailendra Kumar
*Attorney, Agent, or Firm*—Nixon & Vanderhye

[57] ABSTRACT

A compound bearing at least two 2,6-diiodophenyl-4-yl groups represented by formula (IV), particularly a polymer composed of two to eight iodinated tyrosine molecules condensed with each other. This compound is useful as a diagnostic drug for iodine allergy and the diagnostic methods comprises administering the drug to the patient to examine the intracutaneous reaction

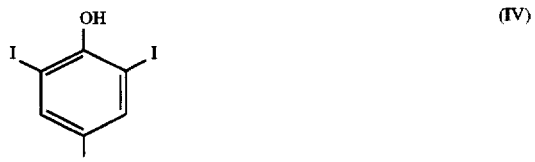

(IV)

15 Claims, No Drawings

COMPOUND BEARING TWO, 2,6-DIIODOPHENOL-4-YL GROUPS AND DIAGNOSTIC DRUG FOR IODINE ALLERGY

This application is a 371 of PCT/JP95/00997, filed May 24, 1995.

|INDUSTRIAL FIELD OF THE INVENTION|

The present invention relates to a compound bearing at least two 2,6-diiodophenyl-4-yl groups having diagnostic activity of iodine allergy. This compound is useful for predicting adverse effect caused by using iodinated X-ray contrast media and other iodine containing drugs.

|DESCRIPTION OF THE PRIOR ART AND BACKGROUND OF THE INVENTION|

X-ray radiograms of the blood-vessel and the urinary tract were widely used today for the purpose of accurate understanding of the condition of diseases and better planning therapeutic programs. The X-ray radiograms are taken by X-ray irradiation just after administering iodinated radiocontrast media by vascular as well as nonvascular routes.

However, iodine-containing X-ray contrast media are known to cause the serious side effects such as shock due to iodine allergy during and after their administration.

Iodine containing drugs other than the X-ray contrast media have been developed and their adverse effects depend on iodine allergy are also known.

As described above, there are clinical problems that serious adverse effects like shock by iodine allergy might happen during and after the administration of iodinated X-ray contrast media. Therefore, the development of X-ray contrast media free from such adverse effects is desired. However, X-ray contrast media absolutely free from such adverse effects have not yet been developed today.

Thus, a small amount of an X-ray contrast medium is previously administered intravenously to a patient before the regular use of the X-ray contrast medium, in order to test for hypersensitivity, if any, to the medium. This pretest is deficient in reliability and there are examples in which side effects are either caused by the pretest amount or in the regular test even in the case of a negative result in the pretest, or in which no abnormality is caused in the regular test even in the case of a positive result in the pretest.

Thus, presently, there is no established method for predicting any severe adverse effects caused by iodine allergy to iodinated.drugs such as iodinated X-ray contrast media, and therefore highly reliable agents for easily diagnosing iodine allergy are desired.

It is possible to design in vivo diagnostic compounds of iodine allergy if a chemical structure of antigenic determinants is made clear. It has been known that immediate type hypersensitivity is provoked by cross-linking IgE antibodies by antigen on the surface of mast cells in the skin followed by releasing histamine and other biological active substances of allergy from the mast cells. Cross-linking of the IgE antibodies is possible by the compounds having at least two antigenic determinants in a molecule (Immunology page 265, Edited by Ivan M. Roitt, Jonathan Brostoff, and David K. Male; Gower Medical publishing Ltd. London, England, 1989). Therefore, iodinated proteins produced by reacting iodine to proteins have diagnostic activity of iodine allergy. However, these are immunogenic because of high molecular weight of these iodinated proteins. Accordingly, it is thought undesirable that an administration of the diagnostic agent of iodine allergy to a patient is simultaneously to sensitize the patient to iodine allergy.

In order to avoid this problem, we have designed the compounds having eliciting antigenicity of iodine allergy but not having sensitizing antigenicity.

|EXPLANATION OF THE PRESENT INVENTION|

We, the inventors of the present invention have studied to obtain agents for diagnosing iodine allergy from such a standpoint that the mechanism by which adverse effects caused by iodinated drugs such as iodinated X-ray contrast media is based on iodine allergy. During our study, however, we have experienced a problem that an administration of the diagnostic agent of iodine allergy to a patient is simultaneously to sensitize the patient to iodine allergy. In order to avoid this problem, we have found that compounds having elicitation antigenicity (antigenicity to elicit an allergic reaction) but not having sensitization antigenicity (antigenicity to induce antibody production or immune lymphocytes) are useful. We have studied such compounds to find novel tyrosine derivatives useful as agents for diagnosing iodine allergy caused by iodinated drugs such as iodinated X-ray contrast media, and have completed the present invention.

Accordingly, the present invention provides a compound bearing at least two 2,6-diiodophenol-4-yl groups represented by formula (IV), particularly a polymer composed of two to eight iodinated tyrosine molecules condensed each other. This compound is useful as a diagnostic drug for iodine allergy and the diagnostic method comprises administering the drug to the patient to examine the intracutaneous reaction.

This invention provides compounds represented by the general formula (I) which contains at least two 2,6-diiodophenol-4-yl groups represented by formula (IV).

Moreover, the compounds represented by the formulas (II), (III), (V), (VI), (VII) or (VIII) are desirable.

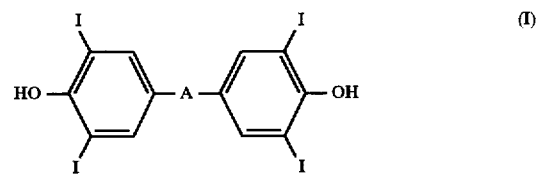

(In the formula, A indicates an atom of two valences or a radical having two valences.)

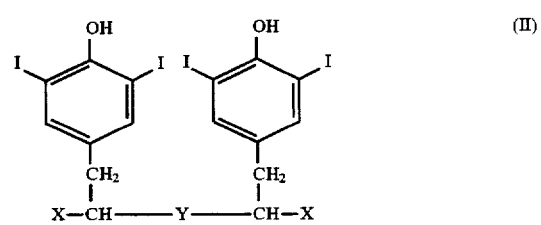

(In the formula (II), X is the same or different and represents an atom or radical of one valence, and Y is an atom of two valences or a radical of two valences.)

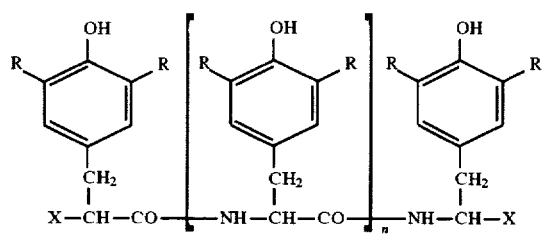
(III)

(In the formula (III), X is the same or different and represents an atom, or radical of one valence. R is the same or different and represents an atom of hydrogen or iodine. n is 0 or 1~6. R is selected as to contain at least two or more radicals represented by formula (IV).)

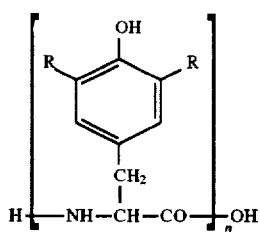
(V)

(In the formula (V), R is the same or different and represents an atom of hydrogen or iodine. n is 2~8 in which R is selected as to contain at least two or more radicals represented by formula (IV).)

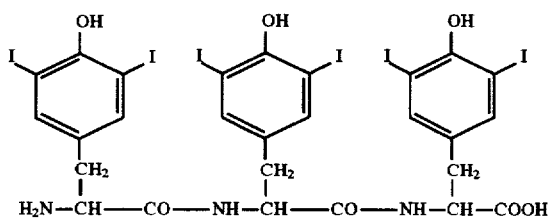
(VI)

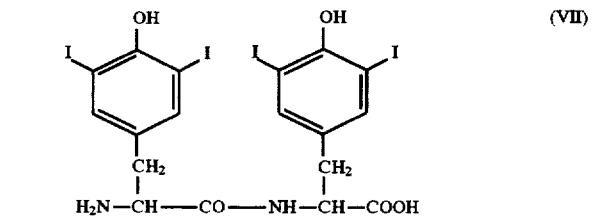
(VII)

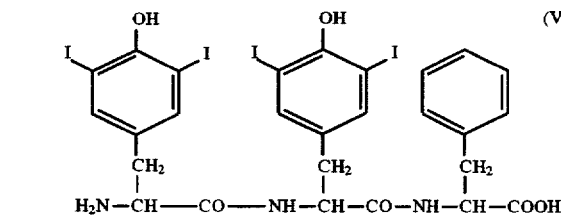
(VIII)

X is preferably amino group, carboxyl group, amino acid group, peptide group, hydrogen or hydroxyl group.

As a substituent, A is preferably —O—, —S—,

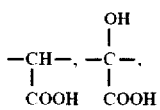

$C_1$~$C_{10}$ alkylene radicals, $C_2$~$C_{10}$ alkenylene radicals, —CO—, —CO—NH—,

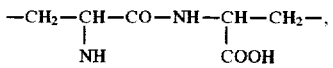

phenylene radical.

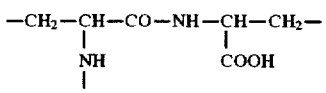

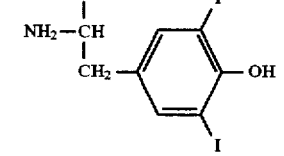

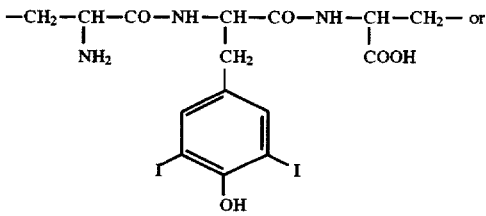

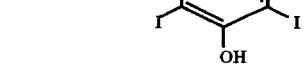

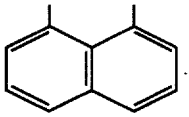

$C_1$~$C_{10}$ alkylene radicals are methylene, ethylene, trimethylene, tetramethylene, pentamethylene, and hexamethylene radicals, etc., and also they may be alkylene radicals with branched-chain such as ethylidene, isopropylidene, ethylethylene, and propylene radicals. $C_2$~$C_{10}$ alkenylene radicals are vinylene, propenylene, 2-butenylene, and 1,3-butadienylene radicals, etc., and they may be branched-chain alkylene radicals such as vinylidene, 4-propyl-2-pentenylene radicals.

Phenylene radicals are

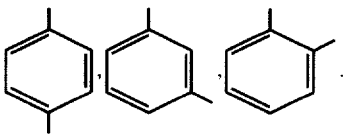

As a substituent, Y is preferably —O—, —S—,

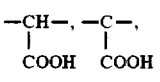

$C_1$~$C_{10}$ alkylene radicals, $C_2$~$C_{10}$ alkenylene radicals, —CO—, —CO—NH—,

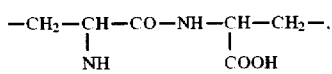

phenylene radical,

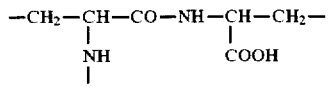
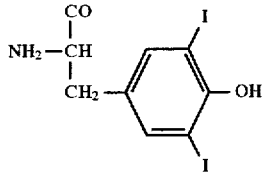

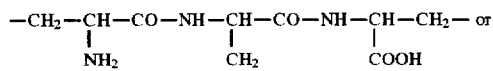
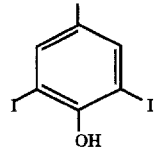

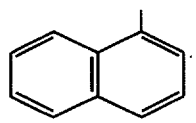

$C_1$~$C_{10}$ alkylene radicals are methylene, ethylene, trimethylene, tetramethylene, pentamethylene, and hexamethylene radicals, etc., and also may be alkylene radicals with branched-chain such as ethylidene, isopropylidene, ethylethylene, and propylene radicals. $C_2$~$C_{10}$ alkenylene radicals are vinylene, propenylene, 2-butenylene, and 1,3-butadienylene radicals, etc., and also may be branched-chain alkylene radicals such as vinylidene, 4-propyl-2-pentenylene radicals.

Phenylene radicals are

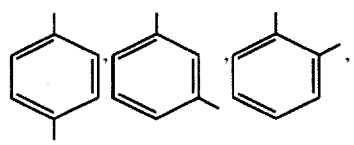

X is —H, —OH, —NH$_2$, —COOH, halogen, $C_1$~$C_{10}$ alkyl radicals, $C_2$~$C_{10}$ alkenyl radicals, $C_2$~$C_{10}$ alkinyl radicals, amino acid group, peptide group, and aryl group. n is 2~6 or 2 or 3. $C_1$~$C_{10}$ alkyl radicals aremethyl, ethyl, propyl, butyl, pentyl, hexyl, heptyl, octyl, nonyl, and decyl radicals and also may be branched-chain alkyl radicals such as 1-methylbutyl and isobutyl radicals. $C_2$~$C_{10}$ alkenyl radicals are vinyl, allyl, propenyl, 2-butenyl, 1,3-butadienyl and 2-pentenyl radicals and also may be branched-chain radicals such as isopropenyl and 3-methyl-2-butenyl radicals. $C_2$~$C_{10}$ alkinyl radicals are ethinyl, 2-propinyl and 2-pentine-4-inyl radicals.

Amino acid groups are aspartic acid, glutamic acid, arginine, histidine, lysine, gultamine, asparagine, cysteine, serine, glycine, and phenylalanine.

Moreover, the present invention offers a diagnostic method for iodine allergy by administering the compounds described above to the patients to examine the intracutaneous reaction. These compounds are injected intradermally at doses of 0.5 to 50 μg before the use of iodinated drugs.

The compounds of the present invention which are represented by general formulae (I)–(VIII) are produced by iodination reaction. For example, a compound saturated with iodine is obtained by reacting 6 mole of iodine molecule to one mole of trityrosine.

Of the compounds of the present invention, these mentioned below are particularly useful agents for diagnosing iodine allergy.

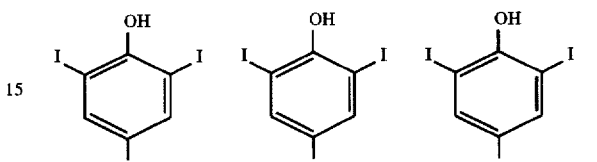

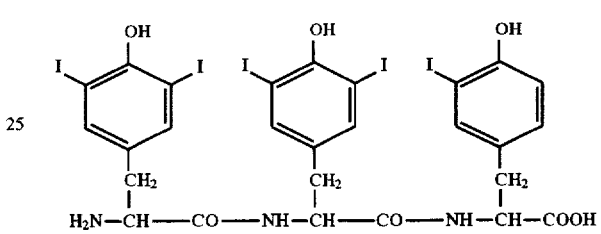

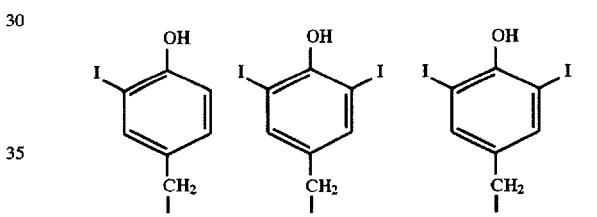

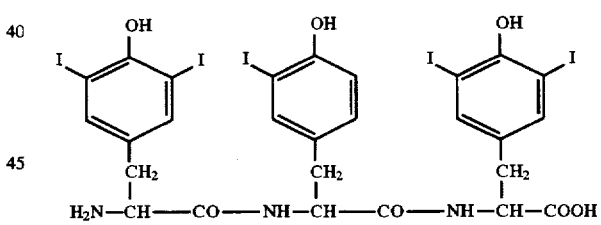

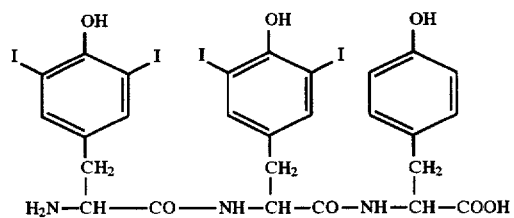

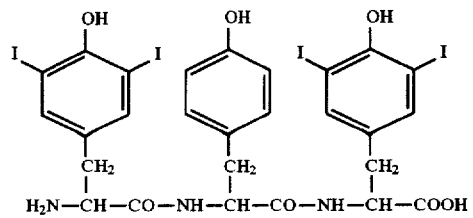

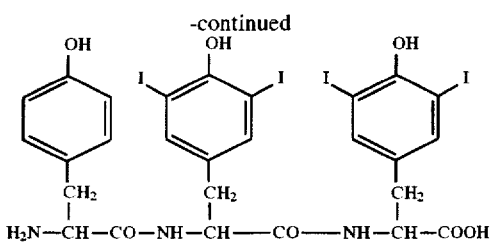

Dityrosine derivative represented by the formula (VII) of the present invention can be produced by reacting iodine to dityrosine. For example, if 4 molecules of iodine are reacted with one mol of dityrosine, the compound represented by the formula (VII) may be obtained.

Of the compounds of the present invention, the compound especially useful as diagnostic drug for iodine allergy is shown bellow.

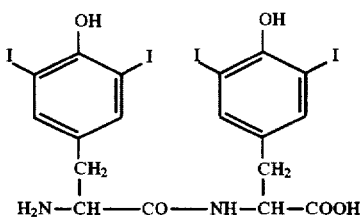

The tyrosine derivative of the present invention represented by the structural formula (VIII) can be obtained by reacting iodine with L-tyrosyl-L-tyrosylphenylalanine. The compound of formula (VIII) can be produced if 4 molecules of iodine are reacted with one mole of L-tyrosyl-L-tyrosylphenylalanine.

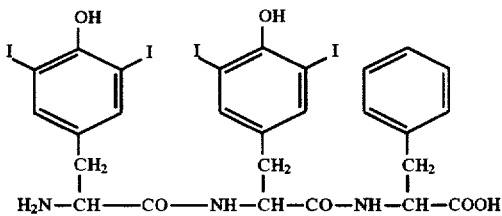

The iodination reaction according to the present invention may be carried out similarly to general iodination reactions by using iodine potassium iodide.

To diagnose the existence, if any, of iodine allergy by using the agent of the present invention, the diagnostic agent is administered to a patient, by intradermal injection before the use of iodinated drugs such as X-ray contrast media, and then the existence, if any, of iodine allergy is diagnosed by the local skin reaction.

The amount of the diagnostic agent of the present invention to be administered is preferably about 0.5 to 50 µg, and more preferably 1 to 10 µg.

The iodinated X-ray contrast media are not limited particularly, provided that they contain iodine atoms, and may include, for example, non-ionic, semi-ionic and ionic iodine-containing X-ray contrast media, such as iopamidol, iohexol, ioversol, iomeprol, iotalane, ioxylan, iodixanol, ioxaglic acid, and sodium iothalamate.

In addition, the diagnostic agents of the present invention can be used for the diagnosis of iodine allergy including side effects caused by iodinated drugs other than iodinated X-ray contrast media.

Since, in most conventional agents for diagnosing allergy, an antigen itself is administered to man, there may be a danger of sensitization caused by the antigen administration.

The present diagnostic compounds have an elicitogenic activity but do not have any sensitizing potency. Accordingly, there is no danger of sensitization by the administration of the compounds for diagnosis of iodine allergy. These facts are illustrated by the following Experimental Example 1 (for elicitation antigenicity) and Experimental Example 2 (for sensitization antigenicity).

|EXPERIMENTAL EXAMPLE 1|

The elicitation antigenicity of iodinated tyrosine derivatives was studied in the bases of the active cutaneous anaphylaxis (ACA) reaction in guinea-pigs immunized with iodine.

Experimental Methods and Experimental Materials

Animals: Male SPF guinea-pigs of Hartley strain, weighing 300–350 g were purchased from Charles River Japan Co., Ltd. These were immunized after having been acclimated for one week.

Sensitization: A solution of iodine potassium iodide (Wako Junyaku, special grade reagent) and complete Freund's adjuvant (Difco) were mixed in equal amounts to form an emulsion. This was administered subcutaneously into the back of guinea-pigs at a dose of 2 mg of iodine per animal 3 times at intervals of 2 weeks. Active cutaneous anaphylaxis (ACA) was elicited 2 weeks after the last sensitization injection.

ACA Induction: 2% Evans blue physiological solution (0.5 ml/animal) was administered intravenously to guinea-pigs, and immediately thereafter 0.1 ml of an elicitation antigen was administered intradermally into the back, and after 30 min. the existence of pigment leakage at the intradermally injected sites was observed.

Elicitation antigen: Iodinated dityrosine, iodinated trityrosine, iodinated dityrosylphenylalanine were administered intracutaneously at 0.1 ml/site. Guinea-pig serum albumin (fraction V: Sigma) was iodinated and used as a positive control. Corresponding noniodinated ones were also administered intradermally as negative controls.

Iodination reaction: To a 50 mM boric acid buffer solution (pH 9.5) of 10 mg/ml of dityrosine, trityrosine, or dityrosylphenylalanine (all produced by Sigma Co., Ltd.) or guinea-pig serum albumin (abbreviated hereafter as GSA), a 0.5M solution of iodine was added at a ratio of 10:1, and these were reacted at 37 C. overnight. The excess iodine in the reaction mixture was reduced by adding sodium thiosulfate (Nakarai Chemical Co., Ltd.). For purification of the iodinated tyrosine derivatives, the reaction mixture was extracted with ethyl acetate and dried with magnesium sulfate, and hexane was added to obtain crystals. For purification of the iodinated GSA, the reaction mixture was purified by passing it through a Sephadex G25 column.

Results

Results of ACA reaction elicited by the iodinated tyrosine derivatives in guinea-pigs sensitized with iodine were shown in Table 1.

Table 1 demonstrated that ACA reaction was elicited by intradermal injection of each of iodinated trityrosine, iodinated dityrosine and iodinated dityrosylphenylalanine in guinea-pigs sensitized with iodine, ACA reaction was also elicited by iodinated guinea-pig serum albumin (iodinated GSA) used as a positive control, whereas the reaction did not occurred by any of iodinated tyrosine derivatives in the non-sensitized guinea-pigs.

Therefore, it is suggested that the iodinated tyrosine derivatives of the present invention have the property of eliciting an allergic reaction in those animals which have been sensitized with iodine.

TABLE 1

Elicitation antigenicity of iodinated tyrosine derivatives

| Elicitation antigen | Dose of antigen (μg/site) | Mean diameter of blue spots (mm) | |
|---|---|---|---|
| | | Iodine-sensitized guinea pig | Non-sensitized guinea-pig |
| Iodinated trityrosine | 100 | 11.0 | 6.0 | —* |
| | 10 | 8.5 | 4.0 | — |
| | 1 | 6.0 | — | — |
| Iodinated dityrosine | 100 | 7.0 | 5.0 | — |
| | 10 | 5.0 | — | — |
| | 1 | — | — | — |
| Iodinated dityrosyl-phenylalanine | 100 | 8.0 | 3.0 | — |
| | 10 | 7.0 | — | — |
| | 1 | — | — | — |
| Iodinated GSA | 100 | 11 | 8.5 | — |
| | 10 | 7.5** | 5.0** | — |
| Trityrosine | 1000 | — | — | — |
| Dityrosine | 1000 | — | — | — |
| Dityrosylphenylalanine | 1000 | — | — | — |
| GSA | 1000 | — | — | — |

*: Negative response
**: Weak response

|EXPERIMENTAL EXAMPLE 2|

Sensitization antigenicity of iodinated tyrosine derivative was studied.

Trityrosine was selected as the tyrosine derivative, and this was iodinated to obtain iodinated trityrosine. Guinea-pigs were sensitized with iodinated trityrosine. As a positive control, employed was iodinated guinea-pig serum albumin (GSA). Guinea-pigs of the control group were sensitized with iodinated GSA. Sensitization was examined by active systemic anaphylaxis (ASA) reaction and passive cutaneous anaphylaxis (PCA) reaction.

Sensitization: Each of iodinated trityrosine and iodinated GSA was emulsified with complete Freund's adjuvant, and injected subcutaneously to the back of animals at a dose of 10 mg/animal (2.5 mg, respectively, at 4 sites), 3 times at intervals of 2 weeks.

ASA reaction: Iodinated GSA (1 mg/animal) was injected intravenously to the animals one week after the last sensitization injection, by which ASA reaction was elicited. The animals which indicated symptoms of anaphylactic shock were judged as being positive.

PCA reaction: The blood was taken from each animal, and the serum was separated one week after the last sensitization injection. The serum was diluted fivefold with physiological saline, and injected intradermally to normal guinea-pigs at a dose of 0.1 ml/site. PCA reaction was provoked by intravenous injection of iodinated GSA (1 mg/animal) and Evans blue solution to the recipient animals 4 hours after the intradermal serum injection. PCA reaction was judged as being positive when the diameter of blue spot at the site of intradermal injection was 5 mm or larger.

Results

The results are shown in Table 2.

As is obvious from the Table 2, ASA reaction and PCA reaction were positive in all animals of the positive control group, i.e., the iodinated guinea-pig serum albumin (iodinated GSA)-sensitized group, while ASA reaction and PCA reaction are both negative in all animals of the iodinated trityrosine-sensitized group. This means that no anti-iodine antibody was produced in the animals sensitized with iodinated trityrosine. From this, it is suggested that iodinated trityrosine has no sensitization antigenicity.

TABLE 2

Sensitization Antigenicity of Iodinated Trityrosine

| Sensitized with | Number of positive animal/Number of sensitized animal | |
|---|---|---|
| | ASA reaction | PCA reaction |
| Iodinated trityrosine | 0/5 | 0/5 |
| Iodinated GSA | 5/5 | 5/5 |

|EXPERIMENTAL EXAMPLE 3|

The present invention is founded on the finding that an antigenic determinant of iodine allergy is diiodotyrosine. It is possible to diagnose iodine allergy by skin test using compounds having 2 or more residues of diiodotyrosine.

The finding that an antigenic determinant of iodine allergy is diiodotyrosine was discovered as the followings.

Guinea-pigs were immunized with iodine by injecting subcutaneously 1 mg of iodine containing potassium iodide solution treated with complete Freund's adjuvant seven times at intervals of 2 weeks, and anti-iodine antiserum was obtained from these animals. Antibody titers of the sera were determined by enzyme linked immunosorbent assay (ELISA) using 96 well microplate coated with iodinated guinea pig serum albumin (I-GSA) ELISA inhibition activities of the following compounds were studied. The compounds used were potassium iodide, tyrosine and its derivatives such as L-tyrosine, monoiodo-L-tyrosine, diiodotyrosine, hexaiodo-L-trityrosine, L-hexatyrosine and 12 iodo-L-hexatyrosine, and iodinated X-ray contrast media such as amidotrizoic acid, iodamide, ioxaglic acid, iohexol, iopamidol and iomeprol.

ELISA inhibition study was performed as follows. Antibody concentration of anti-iodine antiserum gave the maximum optical density in ELISA till one hundredfold serum dilution. Accordingly, seven steps of twofold serial dilution of anti-iodine antiserum, starting from 50-fold serum dilution, were made with physiological saline as a diluent. To each of the serially diluted sera, were added equal volume of solution containing each of the test compounds described above. After overnight incubation at 4 C, antibody activity was determined by ELISA. Phosphate buffered physiological saline (PBS) was used as a control. ELISA inhibitory activities of the test compounds were determined at the serum dilution which gave about 50% of the maximum optical density ($OD_{415nm}=2.6$) of ELISA of control at serum dilution of one hundredfold. The inhibitory activity was calculated by the following calculation formula.

Inhibition rate=[1−Optical density under test compouund/Optical density under PBS]×100%

Inhibition rates were shown in Table 3, and inhibitory activity which was judged from the inhibition rates was described as + if a compound had inhibitory activity and − if a compound did not have inhibitory activity. The results were shown in Table 3.

TABLE 3

ELISA inhibitory activities of compounds on anti-iodine antibody

| Compound | Concentration of compound | ELISA inhibitory activity Inhibition rate (%) | Judgment |
|---|---|---|---|
| Potassium iodide | 10 mM | 0 | − |
| L-Tyrosine | 10 mM | −2.6 | − |
| Monoiodo-L-tyrosine | 10 mM | 5.6 | − |
| Diiodo-L-tyrosine | 10 mM | 100 | + |
| L-Hexatyrosine | 1 mM | 0 | − |
| 12 Iodo-L-hexatyrosine | 1 | 94.3 | + |
| Amidotrizoic acid | 10 mM | 0.3 | − |
| Iodamide | 10 mM | 3.5 | + |
| Ioxaglic acid | 10 mM | −9.4 | + |
| Iohexol | 10 mM | −5.0 | + |
| Iopamidol | 10 mM | −6.5 | + |
| Iomeprol | 10 mM | −1.8 | + |

In the next, ELISA inhibition study was undertaken to determine the potency of ELISA inhibitory activity of active compounds. Serial twofold dilution of each solution of active compounds were performed starting from 20 mM of diiodo-L-tyrosine, 2 mM of 12 iodo-L-hexatyrosine, and 4 mM of hexaiodo-L-trityrosine, respectively, and then equal volume of 50-fold diluted anti-iodine antiserum was added to them. The inhibitory activity was expressed as the concentration which decreased optical density of ELISA to a half ($OD_{50}$) of the control. The results were shown in Table 4.

TABLE 4

ELISA inhibitory activity of diiodotyrosine derivatives on anti-iodine antibody

| Compound | Inhibitory activity ($OD_{50}$) |
|---|---|
| Diiodo-L-tyrosine | 5 mM |
| Hexaiodo-L-trityrosine | 0.125 mM |
| 12 iodo-L-hexatyrosine | 0.125 mM |

The results shown above indicated that inorganic iodide ion was not an antigenic determinant of iodine allergy. It is essential for the antigenic determinant to have a chemical structure in which tyrosine residue is substituted with 2 iodine atoms. Tyrosine residue which is substituted with one iodine atom does not recognized as the antigenic determinant. Furthermore, none of ionic and nonionic iodinated X-ray contrast media has activity of antigenic determinant of iodine allergy.

|EXAMPLES|

The following is a further explanation of the present invention using examples of preparations, though it is needless to say that the present invention is not limited to them.

Example 1

Production of Hexa-iodinated Trityrosine

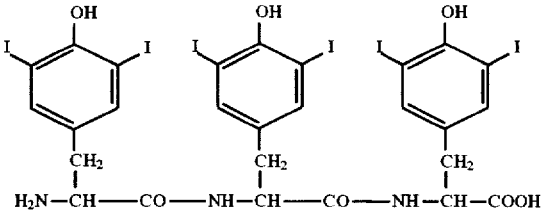

L-Tyr-Tyr-Tyr (250 mg) was added to 20 ml of 50 mM ammonium carbonate buffer (pH 9.4), and dissolved by adding 1N NaOH. To the solution,0.5M iodine potassium iodide (5.6 ml) and 1N NaOH were added little by little, and these were reacted at room temperature for 10 minutes. The non-reacted iodine was decomposed with sodium thiosulfate. Afterwards, 1N HCl was added to the reaction mixture, by which the mixture was adjusted to have pH of 3. The mixture was extracted with ethyl acetate. The extracted ethyl acetate layer was collected, dried with magnesium sulfate and then filtered. This was concentrated with an evaporator, and n-hexane was added to the resulting concentrate. The crystals thus precipitated were taken out by filtration and dried (at 50 C, 30 minutes) to obtain 236 mg of the above-mentioned compound.

Decomposition Point: 170 C $^1$H-NMR ($CD_3OD$) δ (ppm): 2.81(1H, dd, J=10, 15 Hz), 2.89(1H, dd, J=9, 15 Hz) 2.95(1H, dd, J=8, 14 Hz), 3.11(1H, dd, J=5, 15 Hz) 3.13(1H, dd, J=6, 14 Hz), 3.15(1H, dd, J=4, 15 Hz) 4.00(1H, dd, J=4, 9 Hz), 4.61(1H, dd, J=5, 10 Hz) 4.64(1H, dd, J=6, 8 Hz), 7.70(2H, s), 7.73(2H, s), 7.74(2H, s)

MASS (FAB) M+H$^+$=1264

EXAMPLE 2:

Production of Tetra-iodinated Dityrosine

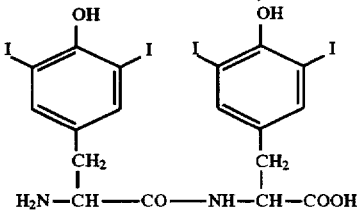

The same process as in Example 1 was repeated, except that L-Tyr-Tyr (317 mg) was used instead of L-Try-Try-Try, to obtain 295 mg of the above-mentioned compound.

Decomposition Point: 160 C $^1$H-NMR ($CD_3OD$) δ (ppm): 2.91(1H, dd, J=10, 15 Hz), 2.95(1H, dd, J=9, 14 Hz) 3.15(1H, dd, J=5, 14 Hz), 3.19(1H, dd, J=5, 15 Hz) 4.03(1H, dd, J=5, 9 Hz), 4.60(1H, dd, J=4, 9 Hz) 7.69(2H, s), 7.76(2H, s)

MASS (FAB) M+H$^+$=849

EXAMPLE 3

Production of 3,5,3',5'-Tetra-iodinated Dityrosylphenylalanine

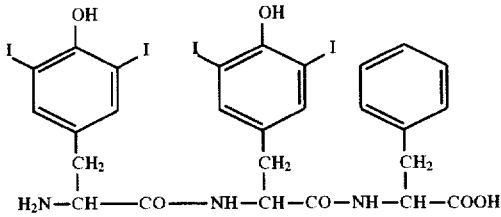

The same process as in Example 1 was repeated, except that L-Tyr-Tyr-Phe (40 mg) was used instead of L-Tyr-Tyr-Tyr, to obtain 43 mg of the above-mentioned compound.

Decomposition Point: 110 C $^1$H-NMR (CD$_3$OD) δ (ppm): 2.77(1H, dd, J=10, 14 Hz), 2.81(1H, dd, J=9, 15 Hz) 3.08(1H, dd, J=8, 14 Hz), 3.10(1H, dd, J=4, 15 Hz) 3.26(1H, dd, J=5, 14 Hz), 3.98(1H, dd, J=4, 9 Hz) 4.65(1H, dd, J=5, 10 Hz), 4.74(1H, dd, J=5, 8 Hz) 7.3(5H, m),7.71(2H, s), 7.74(2H,s)

MASS (FAB) M+H$^+$=996

EXAMPLE 4

Production of Dodeca-iodinated Hexatyrosine

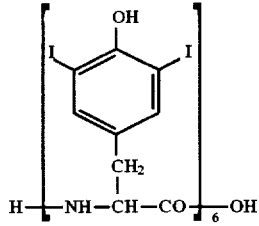

The same process as in Example 1 was repeated, except that L-Tyr-Tyr-Tyr-Tyr-Tyr-Tyr (20 mg) was used instead of L-Tyr-Tyr-Tyr, to obtain 34 mg of the above-mentioned compound.

MASS (FAB) M+H$^+$=2509

We claim:
1. A compound having the formula:

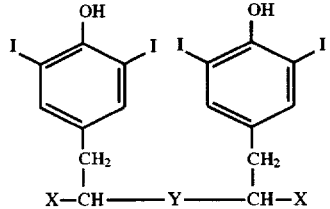

wherein X is the same or different and represents an atom or radical of one valence, and Y is

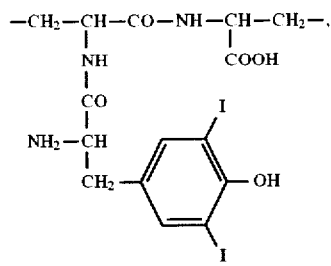

or

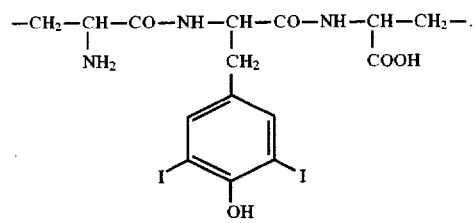

2. A compound having the structural formula:

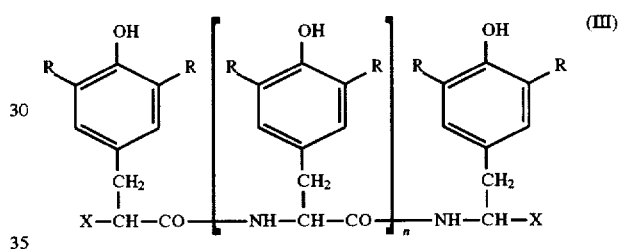

wherein X may be the same or different atom, or the same or different radical of a single valence, R which may be the same or different, is hydrogen or iodine, n is 1 to 6 and contains at least three or more radicals represented by formula (IV)

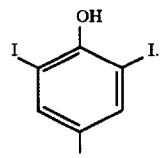

3. A compound having the structural formula:

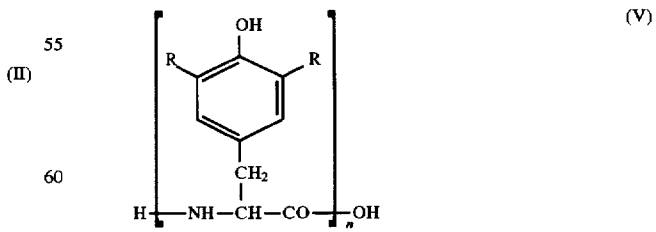

wherein R which may be the same or different is hydrogen or iodine, n is 3 to 8, and contains at least three or more radicals represented by formula (IV)

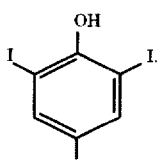

4. A compound having the structural formula:

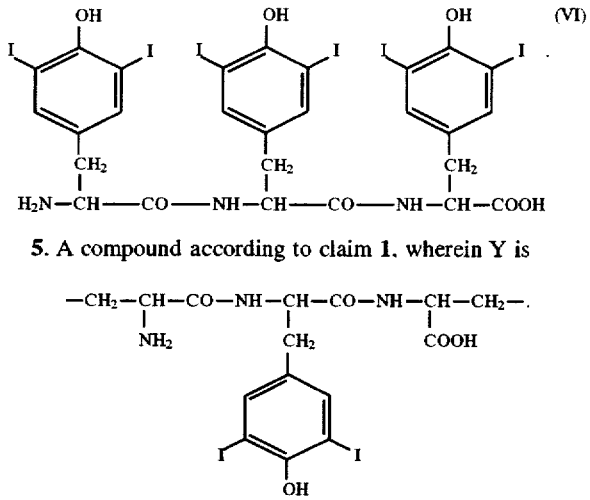

5. A compound according to claim 1, wherein Y is

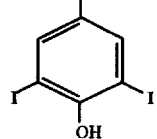

6. A compound according to claim 2, wherein X is —H, —OH, —NH₂, —COOH, halogen, C₁–C₁₀ alkyl radical, C₂–C₁₀ alkenyl radicals, C₂–C₁₀ alkinyl radicals, amino acid radicals, peptide radicals, or aryl radicals.

7. A compound according to claim 3, wherein n is 3 to 6.

8. A compound according to claim 1, wherein X is amino groups, carboxyl groups, amino acid residues, peptide groups, hydrogen or hydroxyl groups.

9. A method of determining a subject's hypersensitivity to iodine comprising administering to said patient by intracutaneous injection an effective amount of a compound of claim 2 and thereafter examining the patient's skin for local skin reaction at the site of injection for an allergic reaction.

10. The method according to claim 9 wherein from 0.5 to 5 µg of said compound is administered to said subject then, in the absence of a reaction, an iodine-containing drug is administered.

11. A pharmaceutical composition comprising a compound of claim 1 together with a pharmaceutically acceptable carrier.

12. A pharmaceutical composition comprising a compound of claim 2 together with a pharmaceutically acceptable carrier.

13. A pharmaceutical composition comprising a compound of claim 3 together with a pharmaceutically acceptable carrier.

14. A pharmaceutical composition comprising a compound of claim 4 together with a pharmaceutically acceptable carrier.

15. A compound according to claim 2 wherein X is —OH, —NH₂ or —COOH.

* * * * *